(12) United States Patent
Tu (10) Patent No.: US 7,564,942 B2
(45) Date of Patent: Jul. 21, 2009

(54) X-RAY CT APPARATUS

(75) Inventor: Tao Tu, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 259 days.

(21) Appl. No.: 11/748,752

(22) Filed: May 15, 2007

(65) Prior Publication Data

US 2007/0268998 A1  Nov. 22, 2007

(30) Foreign Application Priority Data

May 19, 2006  (CN) .................... 2006 1 0082494

(51) Int. Cl.
*A61B 6/03* (2006.01)
(52) U.S. Cl. .......................................... 378/19
(58) Field of Classification Search ............ 378/4, 378/19
See application file for complete search history.

(56) References Cited

U.S. PATENT DOCUMENTS

| | | | |
|---|---|---|---|
| 5,400,379 A * | 3/1995 | Pfoh et al. ............... | 378/19 |
| 5,546,439 A | 8/1996 | Hsieh | |
| 5,946,371 A | 8/1999 | Lai | |
| 6,259,766 B1 * | 7/2001 | Cuppen ............... | 378/19 |
| 6,285,732 B1 | 9/2001 | Hsieh | |
| 6,327,325 B1 | 12/2001 | Hsieh | |
| 6,658,082 B2 * | 12/2003 | Okumura et al. .......... | 378/19 |
| 6,801,594 B1 | 10/2004 | Ali et al. | |
| 6,980,681 B1 | 12/2005 | Hsieh | |
| 7,006,592 B2 | 2/2006 | Ali et al. | |
| 7,342,993 B2 * | 3/2008 | Besson .................. | 378/19 |
| 2002/0071517 A1 * | 6/2002 | Hoffman ............... | 378/19 |
| 2002/0176530 A1 * | 11/2002 | Okumura et al. .......... | 378/19 |

FOREIGN PATENT DOCUMENTS

JP  2005324052  11/2005

* cited by examiner

*Primary Examiner*—Chih-Cheng G Kao
(74) *Attorney, Agent, or Firm*—Armstrong Teasdale LLP (57) ABSTRACT

An X-ray CT apparatus permitting compatibility between the resolution orientation and the coverage orientation at low cost is to be realized. The X-ray CT apparatus uses as the X-ray detector what has a former half channel part and a latter half channel part which are the same in the number of slices and differ in the coverage in the body axis direction of the subject and in slice thickness, and selectively performs scan control in the high resolution mode in which the coverage and the slice thickness are smaller and scan control in the high coverage mode in which the coverage and the slice thickness are larger.

18 Claims, 7 Drawing Sheets

X-RAY CT APPARATUS

CROSS REFERENCE TO RELATED APPLICATIONS

This application claims the benefit of Chinese Patent Application No. 200610082494.8 filed May 19, 2006.

BACKGROUND OF THE INVENTION

The present invention relate to an X-ray CT (computed tomography) apparatus, and more particularly to an X-ray CT apparatus using a multi-slice multi-channel X-ray detector.

An X-ray CT apparatus is so configured as to reconstruct an image on the basis of X-ray detected data obtained by scanning a subject with an X-ray source and an X-ray detector that rotate as opposed to each other. When a multi-slice multi-channel X-ray detector is to be used as the X-ray detector, the coverage in the body axis direction of the subject becomes greater, and therefore the efficiency of scanning is enhanced (see Patent Document 1 for instance).

[Patent Document 1] JP-A No. 2005-324052

The coverage in the body axis direction of the subject is given by the following equation. Hereinafter the body axis direction may be sometimes referred to as the z direction.

$$c = n \times d$$

Here, n is the number of slices of the X-ray detector and d, the slice thickness per slice. The slice thickness d determines the spatial resolution in the z direction. The spatial resolution, given by $1/d$, increases with a decrease in the slice thickness d. Hereinafter the spatial resolution may be sometimes referred to as simply the resolution.

Since the resolution $1/d$ and the coverage c are in a relationship of inverse proportion to each other where the number of slices n is constant, improving the resolution and improving the coverage cannot be compatible. Therefore, a multi-slice multi-channel X-ray detector is produced with emphasis placed on either the resolution or the coverage where the number of slices is given. An X-ray CT apparatus using such an X-ray detector cannot help being either a resolution-oriented X-ray CT apparatus or a coverage-oriented X-ray CT apparatus.

According to Patent Document 1 cited above, compatibility between the resolution orientation and the coverage orientation is sought by so configuring the X-ray detector as to have thinner parts and thicker parts in slice thickness in all the channels, but an X-ray detector having thinner parts and thicker parts in slice thickness in all the channels costs higher.

SUMMARY OF THE INVENTION

It is desirable that the problem described previously is solved.

An X-ray CT apparatus according to one aspect of the invention to solve the problem noted above is an X-ray CT apparatus which, using an X-ray source and a multi-slice multi-channel X-ray detector opposed to each other, collects X-ray detected data by scanning a subject under the control of scan control means, and reconstructs an image with image reconstructing means on the basis of the X-ray detected data, wherein the X-ray detector has a former half channel part and a latter half channel part which are the same in the number of slices and differ in the coverage in the body axis direction of the subject and in slice thickness; the scan control means selectively performs scan control in a high resolution mode in which the coverage and the slice thickness are smaller or scan control in a high coverage mode in which the coverage and the slice thickness are larger; the image reconstructing means, when a scan in the high resolution mode is performed, generates, from real data obtained by the former half channel part (or the latter half channel part) having a larger coverage, data matched with the coverage and the slice thickness of the latter half channel part (or the former half channel part) having a smaller coverage as the data of the former half channel part (or the latter half channel part), combines, with these generated data real data obtained by the latter half channel part (or the former half channel part) having a smaller coverage, and reconstructs an image on the basis of those combined data; and the image reconstructing means, when a scan in the high coverage mode is performed, generates, from real data obtained by the latter half channel part (or the former half channel part) having a smaller coverage, data matched with the slice thickness of the former half channel part (or the latter half channel part) having a larger coverage as the data of the latter half channel part (or the former half channel part), generates, from real data obtained by the former half channel part (or the latter half channel part) having a larger coverage, data regarding a part where no real data can be obtained by the latter half channel part (or the former half channel part) having a smaller coverage, combines, with these generated data, the real data obtained by a part where the coverage is larger, and reconstructs an image on the basis of those combined data.

It is preferable from the viewpoint of appropriately performing data generation for the image reconstructing means to use the Lagrange method for generating, from real data obtained by the former half channel part (or the latter half channel part) having a larger coverage, data matched with the coverage and the slice thickness of the latter half channel part (or the former half channel part) having a smaller coverage, as the data of the former half channel part (or the latter half channel part).

It is preferable from the viewpoint of appropriately performing data generation for the image reconstructing means to use mirror point data for generating, from real data obtained by the former half channel part (or the latter half channel part) having a larger coverage, data regarding a part where no real data can be obtained by the latter half channel part (or the former half channel part) having a smaller coverage.

It is preferable from the viewpoint of effectively performing resolution-oriented scanning for a scan in the high resolution mode to have the coverage of the latter half channel part (or the former half channel part) which is smaller in coverage as the unit coverage.

It is preferable from the viewpoint of effectively performing coverage-oriented scanning for a scan in the high coverage mode to have the coverage of the former half channel part (or the latter half channel part) that is larger in coverage as the unit coverage.

An X-ray CT apparatus according to another aspect of the invention to solve the problem noted above is an X-ray CT apparatus which, using an X-ray source and a multi-slice multi-channel X-ray detector opposed to each other, collects X-ray detected data by scanning a subject under the control of scan control means, and reconstructs an image with image reconstructing means on the basis of X-ray detected data, wherein the X-ray detector has a former half channel part and a latter half channel part which are the same in the coverage in the body axis direction of the subject and differ in the number of slices; the former half channel part (or the latter half channel part) which is smaller in the number of slices is uniform in slice thickness; the latter half channel part (or the former half channel part) larger in the number of slices comprises two portions differing in slice thickness; the number of slices of one of the two portions is the same as the number of slices of the former half channel part (or the latter half channel part) of which the number of slices is smaller, and the slice thickness of the same is thinner than the slice thickness of the former half channel part (or the latter half channel part) of which the number of slices is smaller; and the number of slices of the other of the two portions is smaller than the number of slices of the former half channel part (or the latter half channel part) of which the number of slices is smaller, and the slice thickness of the same is the same as the slice thickness of the former half channel part (or the latter half channel part) of which the number of slices is smaller; the scan control means selectively performs scan control in a high resolution mode in which the coverage and the slice thickness are smaller or scan control in a high coverage mode in which the coverage and the slice thickness are larger; the image reconstructing means, when a scan in the high resolution mode is performed, generates, from real data obtained by the former half channel part (or the latter half channel part) having a smaller number of slices, data matched with the number of slices and the slice thickness of the one portion in the former half channel part (or the latter half channel part) having a larger number of slices as the data of the former half channel part (or the latter half channel part), combines, with these generated data the real data obtained by the one portion in the latter half channel part (or the former half channel part) having a larger number of slices, and reconstructs an image on the basis of those combined data; and the image reconstructing means, when a scan in the high coverage mode is performed, generates, from real data obtained by the one portion in the latter half channel part (or the former half channel part) having a larger number of slices, data matched with the slice thickness of the former half channel part (or the latter half channel part) having a smaller number of slices, as the data of the latter half channel part (or the former half channel part), combines, with these generated data, the real data obtained by the other portion in the latter half channel part (or the former half channel part) having a larger number of slices and the real data obtained by the former half channel part (or the latter half channel part) having a smaller number of slices, and reconstructs an image on the basis of those combined data.

It is preferable from the viewpoint of appropriately performing data generation for the image reconstructing means to use the Lagrange method for generating, from real data obtained by the former half channel part (or the latter half channel part) having a smaller number of slices, data matched with the number of slices and the slice thickness of the one portion in the latter half channel part (or the former half channel part) having a larger number of slices, as the data of the former half channel part (or the latter half channel part).

It is preferable from the viewpoint of effectively performing resolution-oriented scanning for a scan in the high resolution mode to have the coverage of the one of two portions differing in slice thickness in the latter half channel part (or the former half channel part) which is larger in the number of slices as the unit coverage.

It is preferable from the viewpoint of effectively performing coverage-oriented scanning for a scan in the high coverage mode to have the coverage of the former half channel part (or the latter half channel part) that is smaller in the number of slices as the unit coverage.

It is preferable from the viewpoint of efficient performance of scanning for the scan to be a helical scan.

According to that one aspect of the invention to solve the problem noted above, the X-ray CT apparatus, using an X-ray source and a multi-slice multi-channel X-ray detector opposed to each other, collects X-ray detected data by scanning a subject under the control of scan control means, and reconstructs an image with image reconstructing means on the basis of the X-ray detected data, wherein the X-ray detector has a former half channel part and a latter half channel part which are the same in the number of slices and differ in the coverage in the body axis direction of the subject and in slice thickness; the scan control means selectively performs scan control in a high resolution mode in which the coverage and the slice thickness are smaller or scan control in a high coverage mode in which the coverage and the slice thickness are larger; the image reconstructing means, when a scan in the high resolution mode is performed, generates, from real data obtained by the former half channel part (or the latter half channel part) having a larger coverage, data matched with the coverage and the slice thickness of the latter half channel part (or the former half channel part) having a smaller coverage as the data of the former half channel part (or the latter half channel part), combines, with these generated data, real data obtained by the latter half channel part (or the former half channel part) having a smaller coverage, and reconstructs an image on the basis of those combined data; and the image reconstructing means, when a scan in the high coverage mode is performed, generates, from real data obtained by the latter half channel part (or the former half channel part) having a smaller coverage, data matched with the slice thickness of the former half channel part (or the latter half channel part) having a larger coverage as the data of the latter half channel part (or the former half channel part), generates, from real data obtained by the former half channel part (or the latter half channel part) having a larger coverage, data regarding a part where no real data can be obtained by the latter half channel part (or the former half channel part) having a smaller coverage, combines, with these generated data, the real data obtained by a part where the coverage is larger, and reconstructs an image on the basis of those combined data. Therefore, it is enabled to realize an X-ray CT apparatus that can achieve compatibility between the resolution orientation and the coverage orientation at low cost.

According to the other aspect of the invention to solve the problem noted above, the X-ray CT apparatus, using an X-ray source and a multi-slice multi-channel X-ray detector opposed to each other, collects X-ray detected data by scanning a subject under the control of scan control means, and reconstructs an image with image reconstructing means on the basis of X-ray detected data, wherein: the X-ray detector has a former half channel part and a latter half channel part which are the same in the coverage in the body axis direction of the subject and differ in the number of slices; the former half channel part (or the latter half channel part) which is smaller in the number of slices is uniform in slice thickness; the latter half channel part (or the former half channel part) larger in the number of slices comprises two portions differing in slice thickness; the number of slices of one of the two portions is the same as the number of slices of the former half channel part (or the latter half channel part) of which the number of slices is smaller, and the slice thickness of the same is thinner than the slice thickness of the former half channel part (or the latter half channel part) of which the number of slices is smaller; the number of slices of the other of the two portions is smaller than the number of slices of the former half channel part (or the latter half channel part) of which the number of slices is smaller, and the slice thickness of the same is the same as the slice thickness of the former half channel part (or the latter half channel part) of which the number of slices is smaller; the scan control means selectively performs scan control in a high resolution mode in which the coverage and the slice thickness are smaller or scan control in a high coverage mode in which the coverage and the slice thickness are larger; the image reconstructing means, when a scan in the high resolution mode is performed, generates, from real data obtained by the former half channel part (or the latter half channel part) having a smaller number of slices, data matched with the number of slices and the slice thickness of the one portion in the former half channel part (or the latter half channel part) having a larger number of slices as the data of the former half channel part (or the latter half channel part), combines, with these generated data, the real data obtained by the one portion in the latter half channel part (or the former half channel part) having a larger number of slices, and reconstructs an image on the basis of those combined data; and the image reconstructing means, when a scan in the high coverage mode is performed, generates, from real data obtained by the one portion in the latter half channel part (or the former half channel part) having a larger number of slices, data matched with the slice thickness of the former half channel part (or the latter half channel part) having a smaller number of slices as the data of the latter half channel part (or the former half channel part), combines, with these generated data, the real data obtained by the other portion in the latter half channel part (or the former half channel part) having a larger number of slices and the real data obtained by the former half channel part (or the latter half channel part) having a smaller number of slices, and reconstructs an image on the basis of those combined data. Therefore, it is enabled to realize an X-ray CT apparatus which can achieve compatibility between the resolution orientation and the coverage orientation at low cost.

Further objects and advantages of the present invention will be apparent from the following description of the preferred embodiments of the invention as illustrated in the accompanying drawings.

BRIEF DESCRIPTION OF THE INVENTION

DETAILED DESCRIPTION OF THE INVENTION

Figure 1:
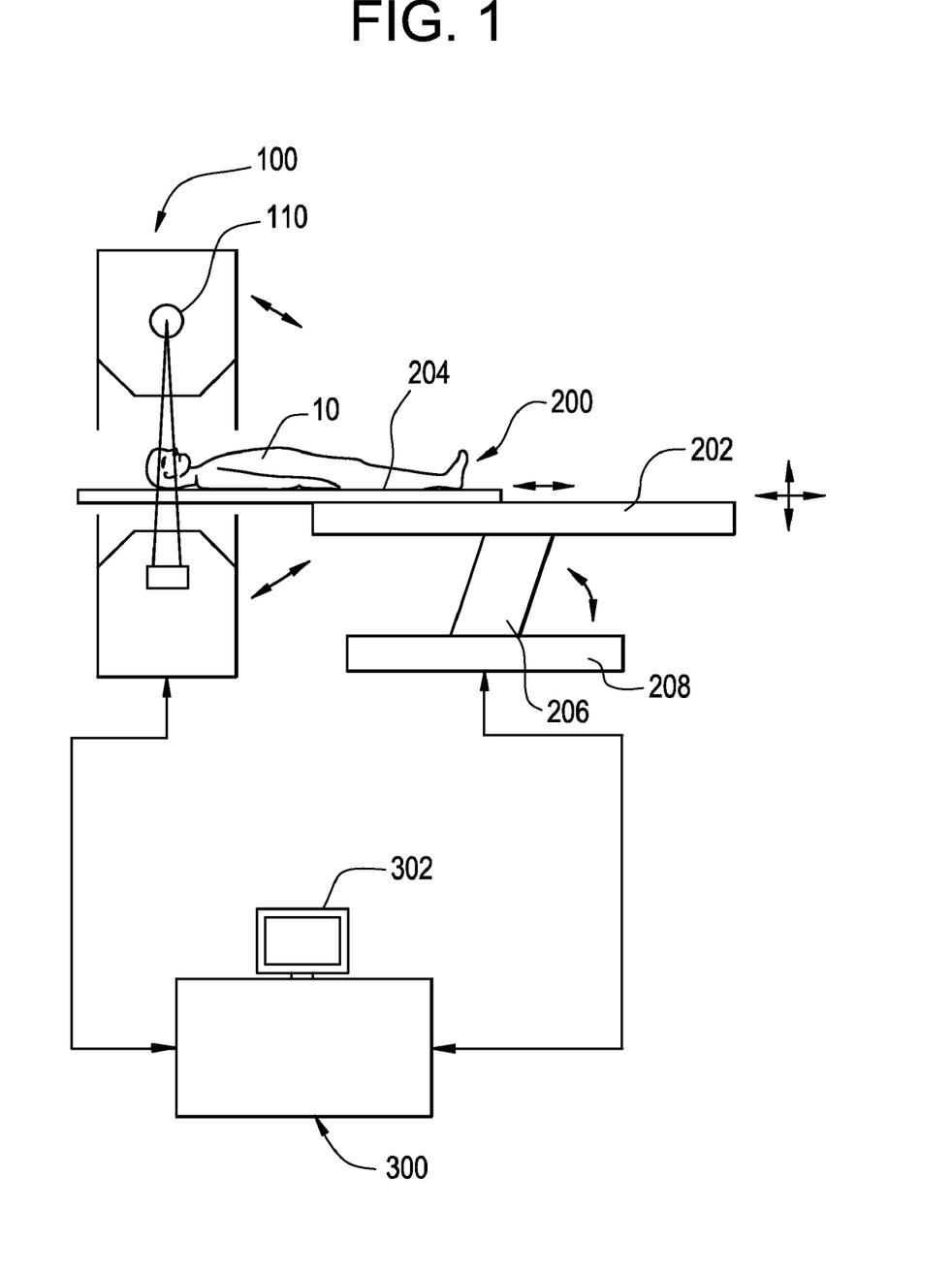
FIG. 1 shows a schematic configuration of an X-ray CT apparatus in one of the best modes for implementing the invention.

The best modes for implementing the invention will be described in further detail below with reference to the accompanying drawings. Incidentally, the present invention is not limited to the best modes for implementing the invention. FIG. 1 shows a schematic configuration of an X-ray CT apparatus. This apparatus is one example of the best modes for implementing the invention. The configuration of this apparatus illustrates one example of the best modes for implementing the invention regarding the X-ray CT apparatus.

This apparatus has a gantry 100, a table 200 and an operator console 300. The gantry 100 collects X-ray detected data in a plurality of views by scanning with an X-ray scanning and detecting device 110 a subject 10 brought in by the table 200, and inputs them to the operator console 300. Hereinafter, the X-ray detected data may be sometimes referred to as scan data.

The operator console 300 carries out image reconstruction on the basis of the scan data inputted from the gantry 100, and displays a reconstructed image on a display 302. The operator console 300 is one example of image reconstructing means according to the present invention.

The operator console 300 controls the actions of the gantry 100 and the table 200. The operator console 300 is one of scan control means according to the invention. Under the control of the operator console 300, the gantry 100 performs scanning under prescribed scan conditions, and the table 200 so positions the subject 10 as to have a prescribed region scanned. The positioning is performed by adjusting the height of a top plate 202 and the horizontal moving distance of a cradle 204 on the top plate with a built-in position adjusting mechanism.

By consecutively performing a plurality of rounds of scanning while continuously moving the cradle 204, helical scanning can be accomplished. By performing scanning in every stopping position while moving the cradle 204 intermittently, cluster scanning can be accomplished. By performing scanning in a position in which the cradle 204 is stopped, axial scanning can be accomplished.

The height of the top plate 202 is adjusted by swinging a support 206 around its fitting portion to a base 208. The swinging of the support 206 displaces the top plate 202 in the vertical direction and the horizontal direction. The cradle 204 moves in the horizontal direction on the top plate 202 to offset the displacement of the top plate 202 in the horizontal direction. Depending on the scan conditions, scanning is performed in a state in which the gantry 100 is tilted. Tilting of the gantry 100 is accomplished by a built-in tilting mechanism.

Figure 2:
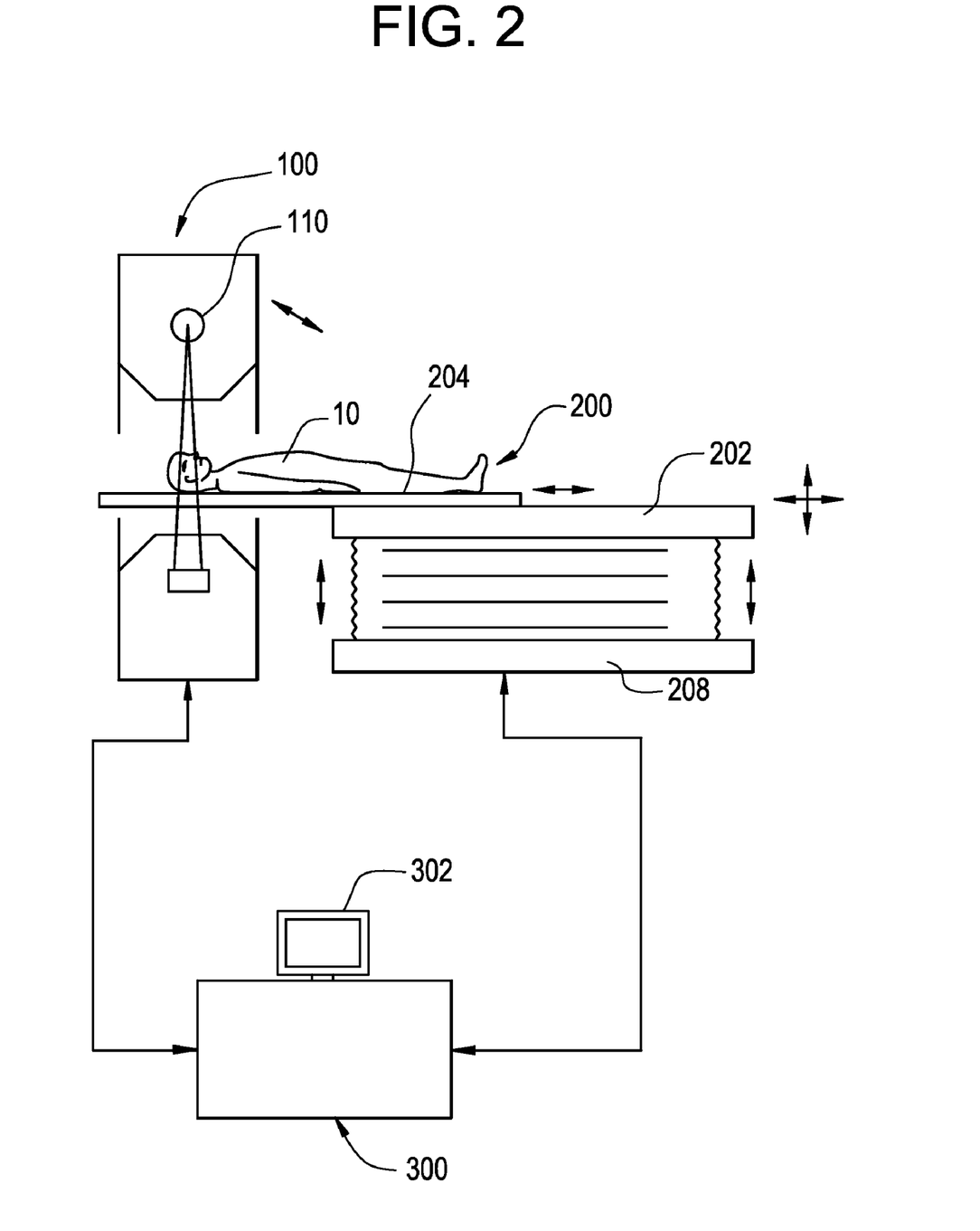
FIG. 2 shows a schematic configuration of an X-ray CT apparatus in another of the best modes for implementing the invention.

Incidentally, the table 200 may be of a type whose top plate 202 rises and falls relative to the base 208 as shown in FIG. 2. The top plate 202 is moved up and down by a built-in elevating mechanism. In this table 200, the moving up or down of the top plate 202 is not accompanied by a horizontal motion.

Figure 3:
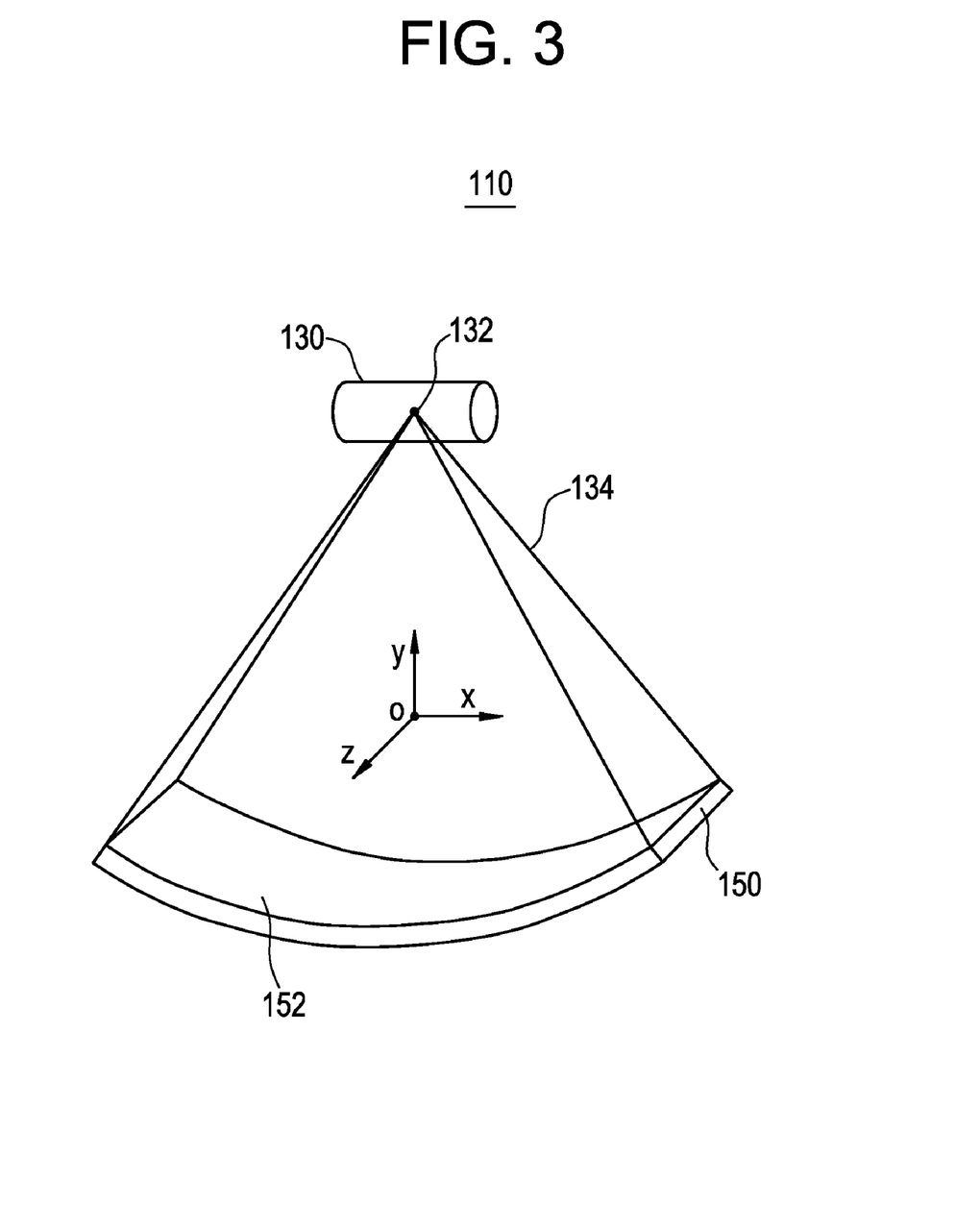
FIG. 3 is a diagram showing the configuration of an X-ray scanning and detecting device.

The configuration of the X-ray scanning and detecting device 110 is shown in FIG. 3. The X-ray scanning and detecting device 110 is so configured as to detect with an X-ray detector 150 X-rays 134 radiated from the focus 132 of an X-ray tube 130. The X-ray tube 130 is an example of X-ray source according to the invention. The X-ray detector 150 is an example of X-ray detector according to the invention.

The X-rays 134 are shaped by a collimator, not shown, into cone beam-shaped X-rays. The X-ray detector 150 has an X-ray incidence face 152 expanding two-dimensionally matching the expansion of the X-rays. The X-ray incidence face 152 is so curved as to constitute part of a cylinder. The center axis of the cylinder passes the focus 132.

The X-ray scanning and detecting device 110 turns around a center axis passing the imaging center, namely the isocenter O. The center axis is parallel to the center axis of a partial cylinder formed by the X-ray detector 150.

The direction of the center axis of rotation is expressed as the z direction, the direction of linking the isocenter O and the focus 132 as the y direction, and a direction normal to the z direction and the y direction as the x direction. These x, y and z axes constitute the three axes of the system of rotating axes having the z axis as its center axis.

Figure 4:
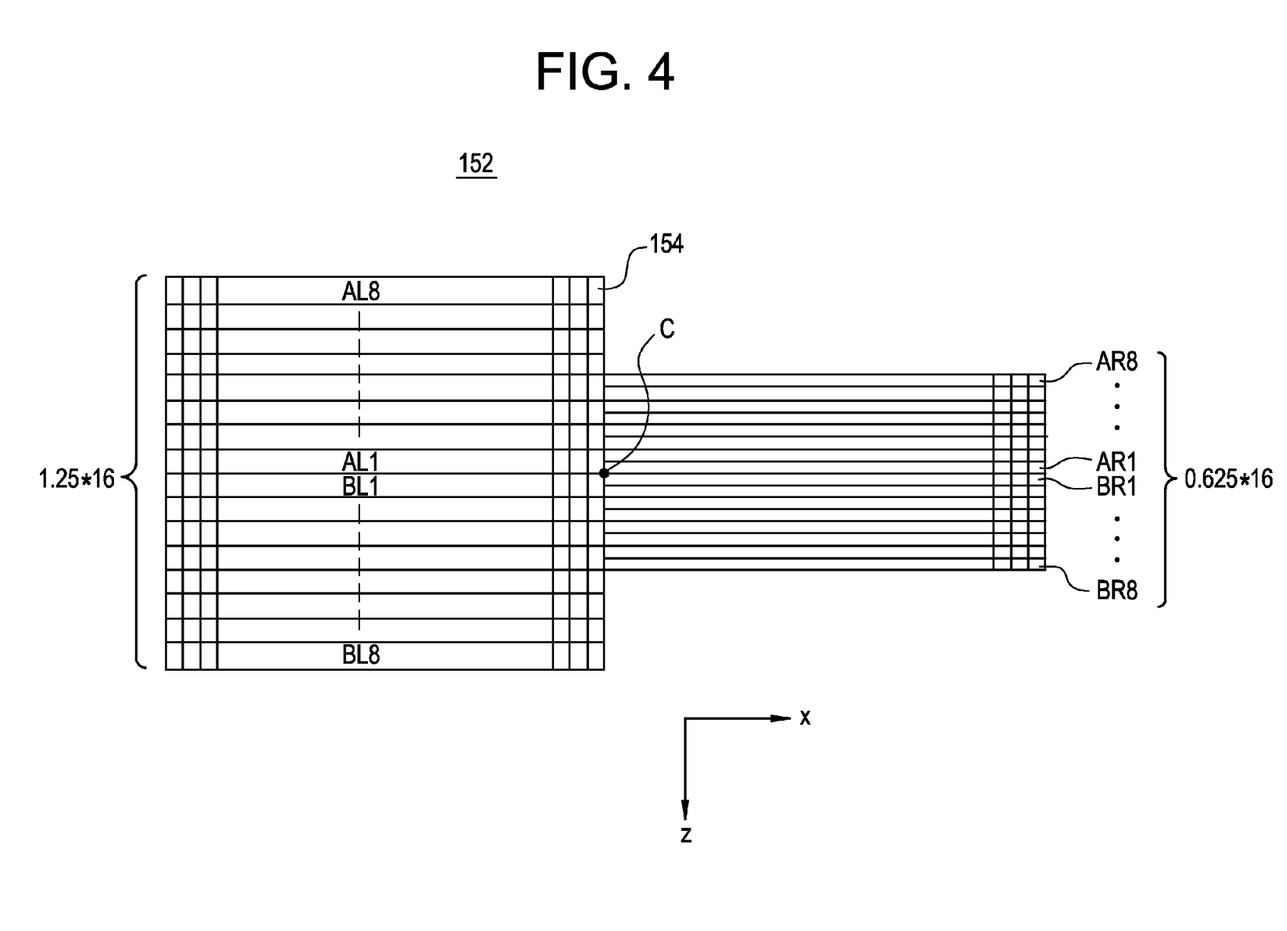
FIG. 4 is a diagram showing the configuration of the X-ray incidence face of an X-ray detector.

FIG. 4 schematically shows a plan of the X-ray incidence face 152. As shown in FIG. 4, the X-ray incidence face 152 has detection cells 154 two-dimensionally arranged in the x direction and the z direction. Thus, the X-ray incidence face 152 constitutes a two-dimensional array of detection cells 154. The detection cells 154 are composed of, for instance, a combination of scintillators and photodiodes.

Individual detection cells 154 constitute detection channels. The detection channels constitute rows consecutive in the x direction. The number of rows is 16 for instance. The number of rows corresponds to the number of slices. In this way, the X-ray detector 150 constitutes a multi-slice multi-channel detector. Incidentally, the number of rows or the number of slices is not limited to 16, but may be any other suitable number such as 32, 64 or 128.

The X-ray incidence face 152 has a center C. The center C is the point where the extension of a straight line linking the focus 132 of X-rays and the isocenter O crosses the X-ray incidence face 152. The X-ray incidence face 152 is divided in the x direction into a left half and a right half with the center C as the boundary.

To assign channel numbers in an ascending order from the left end to the right end, the left half constitutes the former half channel part and the right half, the latter half channel part. Incidentally, if channel numbers are assigned in an ascending order from the right end to the left end, the right half constitutes the former half channel part and the left half, the latter half channel part. In whichever case, the expressions left half and right half are relative ones.

Between the left half and the right half, the width of the detection channel rows differs. Thus on the X-ray incidence face 152, the left and right are asymmetric. The width of the detection channel row in the left half is, for instance, 1.25 mm per row and the width of the detection channel row in the right half is, for instance, 0.625 mm per row.

The detection channel row width corresponds to the slice thickness. Therefore, the slice thickness in the left half is 1.25 mm, and the slice thickness in the right half is 0.625 mm. As a result, between the left half and the right half, the number of rows is the same and the ratio of the row width or the slice thickness is 2:1. Incidentally, the value of the row width or the slice thickness and their ratio are not limited to these values, but may be any other suitable values.

The X-ray incidence face 152 is also divided in the z direction into an upper half and a lower half with the center C as the boundary. Each half has eight detection channel rows. The upper left eight rows are denoted, from in to out, by AL1, ..., AL8. The lower left eight rows are denoted, from in to out, by BL1, ..., BL8. The upper right eight rows are denoted, from in to out, by AR1, ..., AR8. The lower right eight rows are denoted, from in to out, by BR1, ..., BR8. Incidentally, outside AR8 and BR8, there are provided dummy light receiving faces (not shown) having no part in X-ray detection.

This configuration of the X-ray incidence face 152 makes the coverage and the slice thickness in the z direction respectively 1.25*16=20 mm and 1.25 mm in the left half and 0.625*16=10 mm and 0.625 in the right half.

Thus, the X-ray detector 150 has the former half channel part and the latter half channel part that are the same in the number of slices and differ in the coverage in the body axis direction of the subject and in slice thickness. One of the former half channel part and the latter half channel part is smaller, and the other larger, in relative terms in coverage and slice thickness. For this reason, what is smaller in slice thickness becomes a resolution-oriented X-ray detector and what is larger in coverage becomes a coverage-oriented X-ray detector.

To compare this X-ray detector 150 with the X-ray detector described in Patent Document 1, wherein thinner parts and thicker parts in slice thickness are provided in all the channels, the lengths of the thinner parts and the thicker parts in slice thickness of the X-ray detector in the invention are both halved, resulting in a reduced cost.

This apparatus, using such an X-ray detector 150, selectively performs scanning in two different modes. One of the two different modes is a high resolution mode and the other, a high coverage mode. The high resolution mode is the resolution-oriented and the high coverage mode, the coverage-oriented mode.

Figure 5:
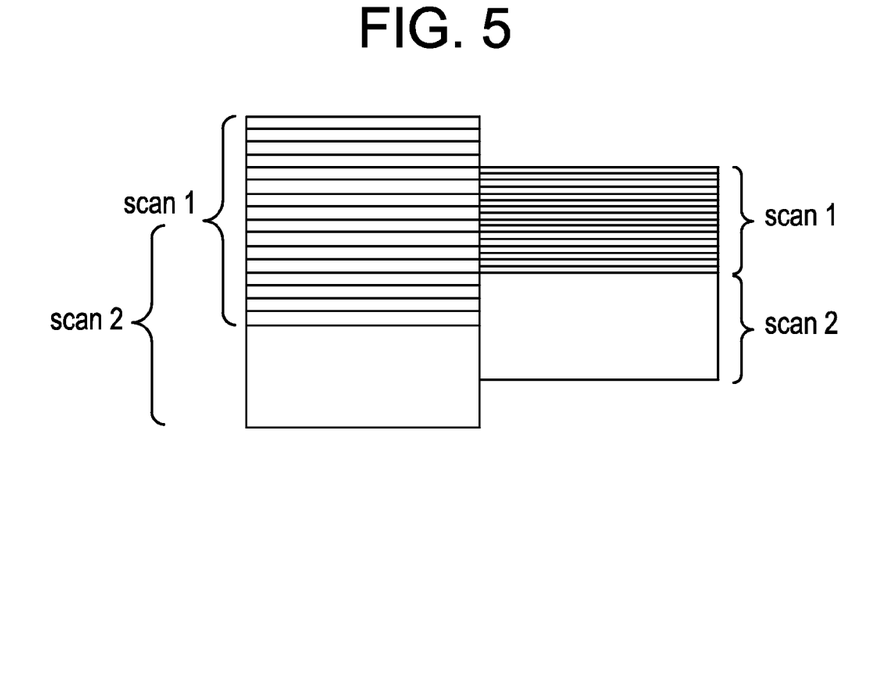
FIG. 5 is a diagram showing high resolution scans.

FIG. 5 schematically shows scans in the high resolution mode. FIG. 5 shows a state in which scans 1 and scans 2 are consecutively performed. As shown in FIG. 5, scans in the high resolution mode are performed coverage by coverage in the right half of the X-ray detector 150. Thus, scans 1 and scans 2 are performed while the scanning position is successively shifted in the z direction as much as the coverage in the right half of the X-ray detector 150 at a time. The same is true of scans 3, 4, ... that follow.

By each scan, scan data of 0.625 mm in slice thickness for 16 slices are obtained at once. However, scan data of 0.625 mm in slice thickness for 16 slices are obtained only for the right half of the X-ray detector 150, but not for the left half of the X-ray detector 150. Hereinafter, the left half of the X-ray detector 150 will be tentatively referred to as the former half channel part and the right half, tentatively as the latter half channel part.

When a 360-degree scan is performed, two coordinate points ($\beta$, $\gamma$) and ($\beta+\pi+2\gamma$, $-\gamma$) are in a relationship of being mirror points of each other on the view-channel plane of the scan data. Here, $\beta$ is the view angle and $\gamma$, the channel angle with reference to the central beam.

A mirror point is a coordinate point having the same X-ray beam path and reverse in direction to a given point when data in the latter's position are to be obtained. Sets of data at such coordinates are referred to as mirror point data. Sets of mirror point data have the same value as each other.

The mirror point of data in the former half channel part are in scan data in the latter half channel part, and the mirror point of data in the latter half channel part are in scan data in the former half channel part.

For this reason, scan data on the view-channel plane have twofold redundancy. To take note of this characteristic, it is possible to reconstruct an image by using data only in half of the view-channel plane. Accordingly in this apparatus, reconstruction of an image equivalent to 16 slices of 0.625 mm in slice thickness is accomplished by using scan data only in the latter half channel part.

Data on all the channels may also be used for image reconstruction. In that case, data equivalent to 16 slices of 0.625 mm in slice thickness [rAL8", ..., rAL1", rBL1", ..., rBL8"] are generated from the data of eight inner detection channel rows AL4, ..., AL1, BL1, ... BL4 [rAL4, ..., rAL1, rBL1, ..., rBL4] in the former half channel part, and those data are combined with data equivalent to 16 slices of 0.625 mm in slice thickness [rAR8, ..., rAR1, rBR1, ..., rBR8] in the latter half channel part. Data equivalent to 16 slices of 0.625 mm in slice thickness [rAL8", rAR8, ..., rAL1", rAR1, rBL1", rBR1, ..., rBL8", rBR8] on all the channels can be thereby obtained.

The data [rAL8", ..., rAL1", rBL1", ..., rBL8"] are generated by decomposing the data equivalent to 16 slices of 1.25 mm in slice thickness [rAL8, . . . , rAL1, rBL1, . . . , rBL8] in the former half channel part into data equivalent to 32 slices of 0.625 mm in slice thickness, and extracting data equivalent to 16 inner slices. For the decomposition of the data, the Lagrange method or the like is used for instance. The Lagrange method is applied to the xz planes of the data.

Since there is a ½ overlap in the coverage of the former half channel part of the scan 1 and the scan 2, data are doubly obtained of this part. Data decomposition can be achieved more accurately by applying the Lagrange method to these double data.

By reconstructing an image by using all-channel data equivalent to 16 slices of 0.625 mm in slice thickness [rAL8", rAR8, . . . , rAL1", rAR1, rBL1", rBR1, . . . , rBL8", rBR8] thereby obtained, a reconstructed image of higher quality can be obtained than when scan data only in the latter half channel part are used.

Figure 6:
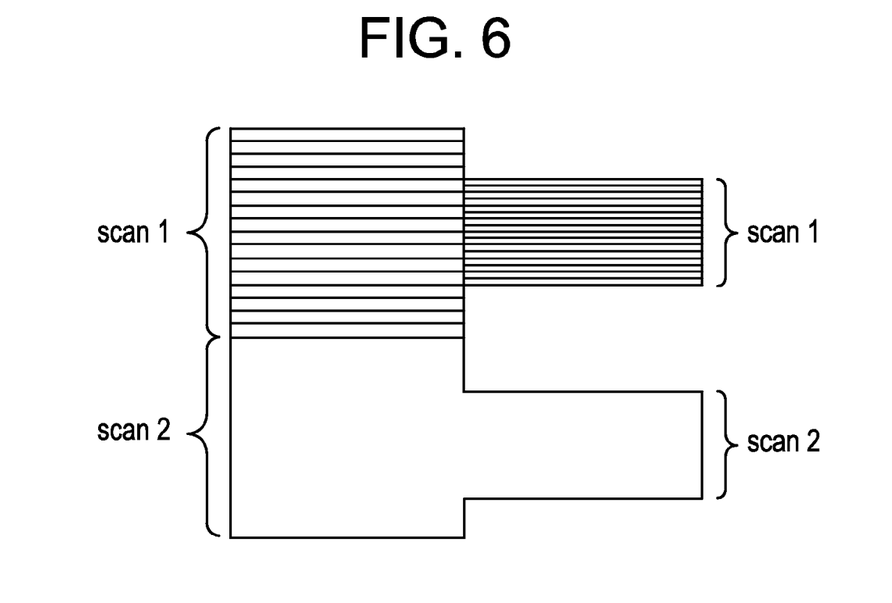
FIG. 6 is a diagram showing high coverage scans.

FIG. 6 schematically shows scans in the high coverage mode. FIG. 6 shows a state in which scans 1 and scans 2 are consecutively performed. As shown in FIG. 6, scans in the high coverage mode are performed coverage by coverage in the left half of the X-ray detector 150. Thus, scans 1 and scans 2 are performed while the scanning position is successively shifted in the z direction as much as the coverage in the left half of the X-ray detector 150 at a time. The same is true of scans 3, 4, . . . that follow.

Each scan gives at once data equivalent to 16 slices of 1.25 mm in slice thickness. However, it is only for the former half channel part of the X-ray detector 150 that data equivalent to 16 slices of 1.25 mm in slice thickness, but not for the latter half channel part of the X-ray detector 150.

Then, with note taken of the redundancy of data on the view-channel plane, reconstruction of an image equivalent to 16 slices of 1.25 mm in slice thickness is accomplished by using data only of the former half channel part.

Data on all the channels may also be used for image reconstruction. In that case, data equivalent to eight inner slices of 1.25 mm in slice thickness [rAR4', . . . , rAR1', rBR1', . . . , rBR4'] in the latter half channel part are generated from the data of 16 slices of 0.625 in slice thickness [rAR8, . . . , rAR1", rBR1, . . . , rBR8] in the latter half channel part. These data are generated by merging a two-slice equivalent each of the data equivalent to 16 slices of 0.625 mm in slice thickness [rAR8, . . . , rAR1, rBR1, . . . , rBR8] in the latter half channel part.

The data [rAR4', . . . , rAR1', rBR1', . . . , rBR4'] so obtained are combined with data equivalent to eight inner slices of 1.25 mm in slice thickness [rAL4, . . . , rAL1, rBL1, . . . , rBL4] in the former half channel part. In this way, data of all the channels of 1.25 mm in slice thickness [rAL4, rAR4', . . . , rAL1, rAR1', rBL1, rBR1', . . . , rBL4, rBR4'] are obtained with respect to the eight inner slices.

For the eight unmeasured slices on the two outer sides of the latter half channel part, data [rAR8', . . . , rAR5', rBR5', . . . , rBR8'] are figured out. These data are obtained by extracting mirror point data out of the data [rAL8, . . . , rAL5, rBL5, . . . , rBL8] equivalent to eight slices in the former half channel part.

By combining them with data equivalent to eight slices in the former half channel part, data [rAL8, rAR8', . . . , rAL5, rAR5', rBL5, rBR5', . . . , rBL8, rBR8'] of 1.25 mm in slice thickness on all the channels can be obtained with respect to the eight outer slices.

By combining the data of the eight outer slices and the data of the eight inner slices, data [rAL8, rAR8', . . . , rAL5, rAR5', rAL4, rAR8+rAR7, . . . , AL1, rAR2+rAR1, BL1, rBR2+rBR1, . . . , rBL4, rBR8+rBR7, . . . rBL5, rBL5' . . . , rBL8, rBR8'] of 1.25 mm in slice thickness on all the channels can be obtained with respect to 16 slices.

By performing image reconstruction by using the data [rAL8, rAR8', . . . , rAL5, rAR5', rAL4, rAR8+rAR7, . . . , AL1, rAR2+rAR1, BL1, rBR2+rBR1, . . . , rBL4, rBR8+rBR7, . . . rBL5, rBR5' . . . , rBL8, rBR8'] equivalent to 16 slices of 1.25 mm in slice thickness on all the channels obtained in this way, a reconstructed image of higher quality can be obtained than when scan data only in the former half channel part are used.

Figure 7:
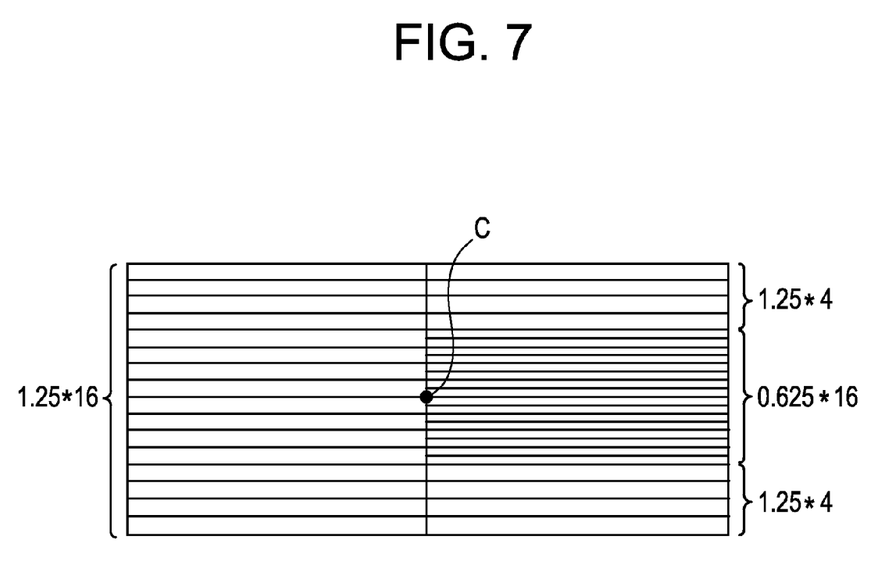
FIG. 7 is a diagram showing the configuration of the X-ray incidence face of an X-ray detector.

FIG. 7 schematically shows another configuration of the X-ray incidence face 152 of the X-ray detector 150. As shown in FIG. 7, the former half channel part of the X-ray detector 150 is the same as what is shown in FIG. 4, while the latter half channel part has four each of detector channel rows of 1.25 mm in slice thickness on both outsides of detector channel rows equivalent to 16 slices of 0.625 mm in slice thickness.

Thus, the X-ray detector 150 has the former half channel part and the latter half channel part that are the same in the coverage in the body axis direction of the subject and differ in the body axis direction of the subject. Namely, the X-ray detector 150 is asymmetric between left and right. In the former half channel part where the number of slices is smaller, the slice thickness is uniform, while the latter half channel part where the number of slices is larger consists of two portions differing in slice thickness.

The inner of the two portions is the same in the number of slices as the former half channel part and thinner in slice thickness than the former half channel part. The outer of the two portions is smaller in the number of slices than the former half channel part and the same in slice thickness as the former half channel part.

Although this X-ray detector 150 corresponds to an X-ray detector of which only the latter half channel part is configured similarly to what is disclosed in Patent Document 1, its manufacturing cost is reduced correspondingly to the configuration in which the thinner part and the thicker part in slice thickness extend over only a half of the channels.

By using such an X-ray detector 150, scanning in the high resolution mode or scanning in the high coverage mode is selectively performed in the same way as described above. And in each mode, image reconstruction is accomplished in the same way as described above.

However, since the latter half channel part has four detection channel rows of 1.25 mm in slice thickness on both outsides, real data in this part can be used when in the high coverage mode. Therefore, there is no need to extract mirror point data from the scan data in the former half channel part. Also, the quality of the image is enhanced because real data are used for image reconstruction.

Figure 8:
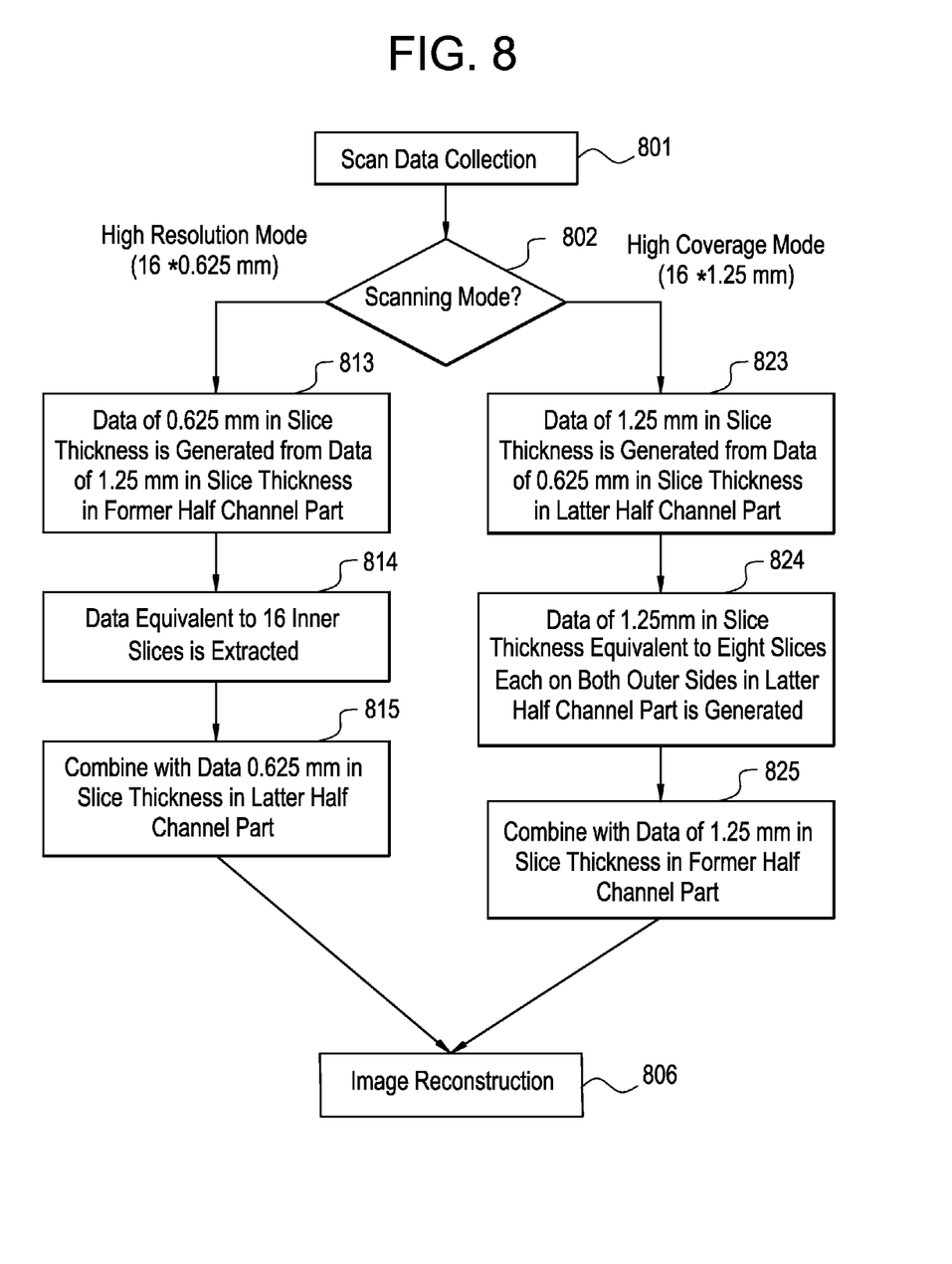
FIG. 8 is a flow chart of the operation of the X-ray CT apparatus in one of the best modes for implementing the invention.

FIG. 8 shows a flow chart of image reconstruction. As shown in FIG. 8, scan data are collected at step 801 and the scanning mode is determined at step 802.

If the scanning mode is the high resolution mode, data of 0.625 mm in slice thickness are generated from the data of 1.25 mm in slice thickness in the former half channel part at step 813. The generation of data is accomplished by using, for instance, the Lagrange method or the like. Data of 0.625 mm in slice thickness equivalent to 32 slices are obtained.

At step 814, data equivalent to 16 inner slices are extracted from the data of 0.625 mm in slice thickness equivalent to 32 slices.

At step 815, by combining them with the data of the latter half channel part, all-channel data of 0.625 mm in slice thickness equivalent to 16 slices are generated.

At step 806, image reconstruction is accomplished by using those data. Tomograms of 16 slices of 0.625 mm in slice thickness, namely high resolution images, are thereby obtained.

If the scanning mode is the high coverage mode, data of 1.25 mm in slice thickness are generated from the data of 0.625 mm in slice thickness in the latter half channel part at step 823. The data generation is accomplished by merging two slices at a time. Data of 1.25 mm in slice thickness equivalent to eight inner slices are thereby obtained.

At step 824, data of 1.25 mm in slice thickness equivalent to eight slices each on both outer sides in the latter half channel part are generated. The data generation is accomplished by extracting mirror point data from the data in the former half channel part. Incidentally, when the X-ray detector shown in FIG. 7 is used, this processing is unnecessary.

At step 825, those data are combined with the data in the former half channel part to generate all-channel data of 1.25 mm in slice thickness equivalent to 16 slices.

At step 806, image reconstruction is accomplished by using those data. Tomograms of 16 slices of 1.25 mm in slice thickness, namely high coverage images, are thereby obtained.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus which, using an X-ray source and a multi-slice multi-channel X-ray detector opposing each other, collects X-ray detected data by scanning a subject under the control of a scan control device, and reconstructs an image with an image reconstructing device on the basis of the X-ray detected data, wherein:

said X-ray detector has a former half channel part and a latter half channel part which are the same in the number of slices and differ in the coverage in the body axis direction of the subject and in slice thickness;

said scan control device selectively performs scan control in a high resolution mode in which the coverage and the slice thickness are smaller or scan control in a high coverage mode in which the coverage and the slice thickness are larger;

said image reconstructing device, when a scan in the high resolution mode is performed, generates, from real data obtained by the former half channel part (or the latter half channel part) having a larger coverage, data matched with the coverage and the slice thickness of the latter half channel part (or the former half channel part) having a smaller coverage, combines real data obtained by the latter half channel part (or the former half channel part) having a smaller coverage with the generated data, and reconstructs an image on the basis of those combined data; and said image reconstructing device, when a scan in the high coverage mode is performed, generates, from real data obtained by the latter half channel part (or the former half channel part) having a smaller coverage, data matched with the slice thickness of the former half channel part (or the latter half channel part) having a larger coverage, generates, from real data obtained by the former half channel part (or the latter half channel part) having a larger coverage, data regarding a part where no real data can be obtained by the latter half channel part (or the former half channel part) having a smaller coverage, combines, with these generated data, the real data obtained by a part where the coverage is larger, and reconstructs an image on the basis of the combined data.

2. The X-ray CT apparatus according to claim 1, wherein:
said image reconstructing device uses the Lagrange method for generating, from real data obtained by the former half channel part (or the latter half channel part) having a larger coverage, data matched with the coverage and the slice thickness of the latter half channel part (or the former half channel part) having a smaller coverage.

3. The X-ray CT apparatus according to claim 1, wherein:
said image reconstructing device uses mirror point data for generating, from real data obtained by the former half channel part (or the latter half channel part) having a larger coverage, data regarding a part where no real data can be obtained by the latter half channel part (or the former half channel part) having a smaller coverage.

4. The X-ray CT apparatus according to claim 1, wherein:
a scan in said high resolution mode has the coverage of the latter half channel part (or the former half channel part) which is smaller in coverage as the unit coverage.

5. The X-ray CT apparatus according to claim 1, wherein:
a scan in said high coverage mode has the coverage of the former half channel part (or the latter half channel part) which is larger in coverage as the unit coverage.

6. The X-ray CT apparatus according to claim 1, wherein: said scan is a helical scan.

7. The X-ray CT apparatus according to claim 2, wherein: said scan is a helical scan.

8. The X-ray CT apparatus according to claim 3, wherein: said scan is a helical scan.

9. The X-ray CT apparatus according to claim 4, wherein: said scan is a helical scan.

10. The X-ray CT apparatus according to claim 5, wherein: said scan is a helical scan.

11. An X-ray CT apparatus which, using an X-ray source and a multi-slice multi-channel X-ray detector opposing each other, collects X-ray detected data by scanning a subject under the control of a scan control device, and reconstructs an image with an image reconstructing device on the basis of X-ray detected data, wherein:

said X-ray detector has a former half channel part and a latter half channel part which are the same in the coverage in the body axis direction of the subject and differ in the number of slices;

the former half channel part (or the latter half channel part) which is smaller in the number of slices is uniform in slice thickness;

the latter half channel part (or the former half channel part) larger in the number of slices comprises two portions differing in slice thickness;

the number of slices of one of the two portions is the same as the number of slices of the former half channel part (or the latter half channel part) of which said number of slices is smaller, and the slice thickness of the said one of the two portions is thinner than the slice thickness of the former half channel part (or the latter half channel part) of which said number of slices is smaller;

the number of slices of the other of the two portions is smaller than the number of slices of the former half channel part (or the latter half channel part) of which said number of slices is smaller, and the slice thickness of the said other one of the two portions is the same as the slice thickness of the former half channel part (or the latter half channel part) of which said number of slices is smaller;

said scan control device selectively performs scan control in a high resolution mode in which the coverage and the slice thickness are smaller or scan control in a high coverage mode in which the coverage and the slice thickness are larger;

said image reconstructing device, when a scan in the high resolution mode is performed, generates, from real data obtained by the former half channel part (or the latter half channel part) having a smaller number of slices, data matched with the number of slices and the slice thickness of said one portion in the former half channel part (or the latter half channel part) having a larger number of slices, combines, with these generated data, the real data obtained by said one portion in the latter half channel part (or the former half channel part) having a larger number of slices, and reconstructs an image on the basis of those combined data; and said image reconstructing device, when a scan in the high coverage mode is performed, generates, from real data obtained by said one portion in the latter half channel part (or the former half channel part) having a larger number of slices, data matched with the slice thickness of the former half channel part (or the latter half channel part) having a smaller number of slices, combines, with these generated data, the real data obtained by said other portion in the latter half channel part (or the former half channel part) having a larger number of slices and the real data obtained by the former half channel part (or the latter half channel part) having a smaller number of slices, and reconstructs an image on the basis of those combined data.

12. The X-ray CT apparatus according to claim 11, wherein:

said image reconstructing device uses the Lagrange method for generating, from real data obtained by the former half channel part (or the latter half channel part) having a smaller number of slices, data matched with the number of slices and the slice thickness of said one portion in the latter half channel part (or the former half channel part) having a larger number of slices.

13. The X-ray CT apparatus according to claim 11, wherein:

a scan in said high resolution mode has the coverage of said one of two portions differing in slice thickness in the latter half channel part (or the former half channel part) which is larger in the number of slices as the unit coverage.

14. The X-ray CT apparatus according to claim 11, wherein:

a scan in said high coverage mode has the coverage of the former half channel part (or the latter half channel part) which is smaller in the number of slices as the unit coverage.

15. The X-ray CT apparatus according to claim 11, wherein:

said scan is a helical scan.

16. The X-ray CT apparatus according to claim 12, wherein:

said scan is a helical scan.

17. The X-ray CT apparatus according to claim 13, wherein:

said scan is a helical scan.

18. The X-ray CT apparatus according to claim 14, wherein:

said scan is a helical scan.

* * * * *